(12) United States Patent
Uitenbroek et al.

(10) Patent No.: US 6,914,018 B1
(45) Date of Patent: Jul. 5, 2005

(54) BIAXIAL STRETCH, BREATHABLE LAMINATE WITH CLOTH-LIKE AESTHETICS AND METHOD FOR MAKING SAME

(75) Inventors: Duane Girard Uitenbroek, Little Chute, WI (US); Michael Tod Morman, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 37 days.

(21) Appl. No.: 09/698,118

(22) Filed: Oct. 27, 2000

(51) Int. Cl.$^7$ .............. D04H 1/00; B32B 25/00
(52) U.S. Cl. .......... 442/59; 442/362; 442/399; 442/400; 442/401; 442/394
(58) Field of Search .............. 442/394, 362, 442/399, 400, 401

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,949,128 A | 4/1976 | Ostermeier |
| 4,100,324 A | 7/1978 | Anderson et al. |
| 4,340,563 A | 7/1982 | Appel et al. |
| 4,443,511 A | 4/1984 | Worden et al. |
| 4,542,199 A | 9/1985 | Kaminsky et al. |
| 4,543,099 A | 9/1985 | Bunnelle et al. |
| 4,606,964 A | 8/1986 | Wideman |
| 4,640,726 A | 2/1987 | Sallee et al. |
| 4,687,477 A | 8/1987 | Suzuki et al. |
| 4,692,369 A | 9/1987 | Nomi |
| 4,701,176 A | 10/1987 | Wilson et al. |
| 4,704,114 A | 11/1987 | Wilson et al. |

(Continued)

FOREIGN PATENT DOCUMENTS

| | | |
|---|---|---|
| EP | 0 236 032 | 12/1992 |
| EP | 0 386 816 | 4/1994 |
| EP | 0 400 111 | 8/1994 |
| EP | 0 451 705 | 8/1994 |
| EP | 0 630 630 | 12/1994 |
| EP | 0 630 631 | 12/1994 |
| EP | 0 630 632 | 12/1994 |
| EP | 0 420 256 | 5/1995 |
| EP | 0 650 714 A | 5/1995 |
| EP | 0 707 106 | 4/1996 |

(Continued)

OTHER PUBLICATIONS

Kadolph et al, Textiles, 1998, Prentice Hall Inc., 8$^{th}$ Edition, pp. 76, 395.*

*Primary Examiner*—Glenn Caldarola
*Assistant Examiner*—Alexis Wachtel
(74) *Attorney, Agent, or Firm*—Pauley Petersen & Erickson (57) ABSTRACT

A breathable laminate having biaxial elastic stretch, cloth-like aesthetics, and a fluid barrier is formed by bonding a breathable elastic film to a nonwoven facing material. The facing material can be inherently machine direction and cross direction stretchable, or can be necked to impart cross direction stretchability, and can be creped or crimped to impart machine direction stretchability. Alternatively, machine direction stretchability of the laminate can be achieved by bonding the elastic film in a pre-stretched condition to the facing material. The breathable laminate is particularly useful as an outer cover for diapers and other personal care products.

32 Claims, 5 Drawing Sheets

U.S. PATENT DOCUMENTS

| | | |
|---|---|---|
| 4,710,187 A | 12/1987 | Boland et al. |
| 4,720,415 A | 1/1988 | Vander Wielen et al. |
| 4,756,709 A | 7/1988 | Stevens |
| 4,770,656 A | 9/1988 | Proxmire et al. |
| 4,801,485 A | 1/1989 | Sallee et al. |
| 4,810,556 A | 3/1989 | Kobayashi et al. |
| 4,813,950 A | 3/1989 | Branch |
| 4,842,596 A | 6/1989 | Kielpikowski et al. |
| 4,863,779 A | 9/1989 | Daponte |
| 4,908,247 A | 3/1990 | Baird et al. |
| 4,938,757 A | 7/1990 | Van Gompel et al. |
| 4,965,122 A | 10/1990 | Morman |
| 4,981,747 A | 1/1991 | Morman |
| 5,036,551 A | 8/1991 | Dailey et al. |
| 5,064,802 A | 11/1991 | Stevens et al. |
| 5,114,781 A | 5/1992 | Morman |
| 5,116,662 A | 5/1992 | Morman |
| 5,143,679 A | 9/1992 | Weber et al. |
| 5,156,793 A | 10/1992 | Buell et al. |
| 5,167,897 A | 12/1992 | Weber et al. |
| 5,171,239 A | 12/1992 | Igaue et al. |
| 5,171,388 A | 12/1992 | Hoffman et al. |
| 5,189,192 A | 2/1993 | LaPointe et al. |
| 5,204,429 A | 4/1993 | Kaminsky et al. |
| 5,226,992 A | 7/1993 | Morman |
| 5,244,482 A | 9/1993 | Hassenboehler, Jr. et al. |
| 5,244,716 A | 9/1993 | Thornton et al. |
| 5,259,902 A | 11/1993 | Muckenfuhs |
| 5,272,236 A | 12/1993 | Lai et al. |
| 5,278,272 A | 1/1994 | Lai et al. |
| 5,336,545 A | 8/1994 | Morman |
| 5,349,100 A | 9/1994 | Mintz |
| 5,352,749 A | 10/1994 | DeChellis et al. |
| 5,354,400 A | 10/1994 | Lavash et al. |
| 5,374,696 A | 12/1994 | Rosen et al. |
| 5,385,775 A | 1/1995 | Wright |
| 5,397,316 A | 3/1995 | LaVon et al. |
| 5,422,172 A | 6/1995 | Wu |
| 5,492,753 A | 2/1996 | Levy et al. |
| 5,496,429 A | 3/1996 | Hasse et al. |
| 5,514,470 A | 5/1996 | Haffner et al. |
| 5,527,302 A | 6/1996 | Endres et al. |
| 5,529,830 A | 6/1996 | Dutta et al. |
| 5,554,143 A | 9/1996 | Roe et al. |
| 5,554,144 A | 9/1996 | Roe et al. |
| 5,554,145 A | 9/1996 | Roe et al. |
| 5,556,394 A | 9/1996 | Roe et al. |
| 5,556,504 A | 9/1996 | Rajala et al. |
| 5,560,878 A | 10/1996 | Dragoo et al. |
| 5,569,232 A | 10/1996 | Roe et al. |
| 5,569,234 A | 10/1996 | Buell et al. |
| 5,582,903 A | 12/1996 | Levy et al. |
| 5,587,225 A | 12/1996 | Griesbach et al. |
| 5,611,790 A | 3/1997 | Osborn, III et al. |
| 5,615,460 A | 4/1997 | Weirich et al. |
| 5,624,422 A | 4/1997 | Allen |
| 5,624,427 A | 4/1997 | Bergman et al. |
| 5,624,729 A | 4/1997 | Cohen et al. |
| 5,628,741 A | 5/1997 | Buell et al. |
| 5,628,856 A | 5/1997 | Dobrin et al. |
| 5,631,074 A | 5/1997 | Herlihy, Jr. |
| 5,635,290 A | 6/1997 | Stopper et al. |
| 5,643,396 A | 7/1997 | Rajala et al. |
| 5,645,672 A | 7/1997 | Dobrin |
| 5,656,167 A | 8/1997 | Martz |
| 5,658,269 A | 8/1997 | Osborn, III et al. |
| 5,660,657 A | 8/1997 | Rajala et al. |
| 5,674,212 A | 10/1997 | Osborn, III et al. |
| 5,683,375 A | 11/1997 | Osborn, III et al. |
| 5,690,627 A | 11/1997 | Clear et al. |
| 5,702,382 A | 12/1997 | Osborn, III et al. |
| 5,713,884 A | 2/1998 | Osborn, III et al. |
| 5,716,478 A | 2/1998 | Boothe et al. |
| 5,749,866 A | 5/1998 | Roe et al. |
| 5,749,989 A | 5/1998 | Linman et al. |
| 5,759,340 A | 6/1998 | Boothe et al. |
| 5,789,065 A | 8/1998 | Haffner et al. |
| 5,804,011 A | 9/1998 | Dutta et al. |
| 5,843,056 A | 12/1998 | Good et al. |
| 5,846,232 A | 12/1998 | Serbiak |
| 5,855,999 A * | 1/1999 | McCormack ............... 428/283 |
| 5,861,074 A | 1/1999 | Wu |
| 5,865,926 A | 2/1999 | Wu et al. |
| 5,883,028 A | 3/1999 | Morman et al. |
| 5,916,663 A * | 6/1999 | Chappell et al. ............. 428/152 |
| 5,921,973 A * | 7/1999 | Newkirk et al. ............ 604/365 |
| 5,928,211 A | 7/1999 | Gustafsson et al. |
| 5,932,497 A | 8/1999 | Morman et al. |
| 6,004,306 A | 12/1999 | Robles et al. |
| 6,028,240 A | 2/2000 | Wessel et al. |
| 6,071,834 A | 6/2000 | Martz |
| 6,129,801 A * | 10/2000 | Benson et al. ............... 156/229 |
| 6,197,404 B1 * | 3/2001 | Varona ........................ 428/152 |
| 6,479,154 B1 * | 11/2002 | Walton et al. ........... 428/424.4 |

FOREIGN PATENT DOCUMENTS

| | | |
|---|---|---|
| EP | 0 433 951 | 8/1996 |
| EP | 0 552 345 | 9/1996 |
| EP | 0 630 221 | 4/1997 |
| EP | 0 409 315 | 5/1997 |
| EP | 0 820 747 | 1/1998 |
| EP | 0 602 613 | 6/1998 |
| EP | 0 651 629 | 6/1998 |
| EP | 0 659 117 | 6/1998 |
| EP | 1 064 895 A | 1/2001 |
| WO | 93/01785 | 2/1993 |
| WO | 93/17648 | 9/1993 |
| WO | 93/21013 | 10/1993 |
| WO | 94/02094 | 2/1994 |
| WO | 96/16625 | 6/1996 |
| WO | 96/18367 | 6/1996 |
| WO | 97/36566 | 10/1997 |
| WO | 97/46198 | 12/1997 |
| WO | 98/29246 | 7/1998 |
| WO | 99/14262 | 3/1999 |
| WO | 99/33424 A1 | 7/1999 |
| WO | 99/33426 A1 | 7/1999 |
| WO | 00/23273 | 4/2000 |
| WO | 00/39201 | 7/2000 |
| WO | 01/15645 A | 3/2001 |

\* cited by examiner

BIAXIAL STRETCH, BREATHABLE LAMINATE WITH CLOTH-LIKE AESTHETICS AND METHOD FOR MAKING SAME

FIELD OF THE INVENTION

This invention is directed to a cloth-like fluid barrier that delivers elasticity in multiple directions and has a controlled level of breathability.

BACKGROUND OF THE INVENTION

A number of various material attributes are desirable for material used to make outer covers of absorbent articles. For example, in pant-like garments, machine direction stretchability is desirable because longitudinal conformability prevents a crotch region of the garment from sagging and bulging. Similarly, cross direction stretchability is desirable because lateral conformability maintains a snug, yet comfortable fit about a wearer's hips. Furthermore, stretchability, more particularly elasticity, in all directions eliminates the need for adding elastic components to a product.

Breathability is a material attribute particularly desirable in absorbent articles. Breathable films and laminates, when used in diapers or similar absorbent garments, reduce the relative humidity and temperature within the garment in comparison to such garments made of non-breathable films and laminates.

A fluid barrier is an inherently desirable material attribute of an absorbent article. The fluid barrier acts to prevent liquids from permeating through a surface of the garment and onto a wearer's clothing.

Cloth-like aesthetics are yet another material attribute particularly desirable for the outer cover of absorbent articles. Materials that have a cloth-like feel and appearance render an absorbent article more comfortable to both a wearer and a care giver. Furthermore, cloth-like materials tend to reduce or eliminate the swishing noise normally associated with non-cloth-like materials used in absorbent articles.

Various types of material with combined attributes are known in the art. For example, stretch-bonded laminates (SBL) deliver a machine direction stretchable, breathable composite, but have no fluid barrier and no stretchability in a cross direction. More recent neck-bonded laminates deliver a cross direction stretchable fluid barrier, but are not stretchable in the machine direction. Other composites claim to be cloth-like, breathable barriers, but they do not stretch in either a machine direction or a cross direction.

U.S. Pat. No. 5,114,781 issued to Morman on May 19, 1992, discloses a laminate that can stretch in at least two directions. The laminate includes a reversibly necked material and an elastic sheet.

U.S. Pat. No. 5,116,662 issued to Morman on May 26, 1992, discloses a laminate that can stretch in at least two directions. The laminate includes a necked material and an elastic sheet.

U.S. Pat. No. 5,883,028 issued to Morman, et al., on Mar. 16, 1999, discloses a laminate that can stretch in at least two directions. The laminate is formed by attaching a nonwoven material that is necked in the cross direction to a water vapor-soluble film that is stretched in the machine direction.

There is a need or desire for a material that delivers a multitude of properties in a single composite, namely high breathability, fluid barrier, cloth-like aesthetics, and biaxial stretch.

SUMMARY OF THE INVENTION

The present invention is directed to a material having high breathability, fluid barrier, cloth-like aesthetics, and biaxial elastic stretch, that is useful as an outer cover for diapers and other personal care products. The material is a laminate formed from a breathable elastic film laminated to a nonwoven facing material that is machine direction and cross direction stretchable.

The film can be created from an inherently breathable elastic polymer (e.g. monolithic films without pores) or can be a microporous film made of any elastic polymer. Suitable films are very lightweight in nature, roughly 5 to 20 gsm, and can deliver breathability, expressed as water vapor transmission rate (WVTR), in a range of about 1,000 to 40,000 grams/$m^2$—24 hours using the Mocon WVTR test procedure described below. Suitable inherently breathable films can include polymers in the thermoplastic polyurethane (TPU) family, the polyether amides family, or the polyester elastomers family.

The machine direction and cross direction extensible nonwoven facing material can be provided by stretching a fibrous nonwoven material in the machine direction to cause necking (and extensibility) in the cross direction. Alternatively, the nonwoven material can be a very loose collection of fibers bonded discontinuously in the cross direction such that the material can be stretched in the cross direction. The same nonwoven material with imparted cross direction extensibility can be crimped or creped in the machine direction to cause machine direction extensibility. Biaxial elasticity in the laminate can also be accomplished by laminating a cross direction extensible nonwoven facing to an elastic film pre-stretched in the machine direction, and allowing the resulting composite to retract, therefore yielding recoverable machine and cross direction elasticity.

The nonwoven facing material can also be made using an elastic polymer which provides the machine direction and cross direction elastic properties. This can be demonstrated by a spunbond nonwoven produced from a thermoplastic elastomer creating an elastic fiber matrix. Suitable polymers for this application can be single-site catalyzed elastomers, such as ethylene-alpha olefin copolymers; thermoplastic polyurethanes; and the like.

The film and the nonwoven facing material can be bonded together, either thermally, via an extrusion coating, with an adhesive, or the like. When optimized layers and processing are utilized, a very "square" laminate is the result, i.e, a. laminate with similar machine direction and cross direction elastic properties.

With the foregoing in mind, it is a feature and advantage of the invention to provide a breathable laminate having biaxial elastic stretch, cloth-like aesthetics, and fluid barrier.

It is also a feature and advantage of the invention to provide an improved breathable laminate useful in a wide variety of diaper outer covers, other personal care products, surgical gowns, and other breathable applications.

The foregoing and other features and advantages of the invention will become further apparent from the following detailed description of the presently preferred embodiments, read in conjunction with the examples and drawings.

DEFINITIONS

Within the context of this specification, each term or phrase below will include the following meaning or meanings.

"Biaxial elastic stretch" refers to stretchability in two directions perpendicular to one another, e.g. stretchability in a machine direction and in a cross direction.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Cross direction" refers to the width of a fabric in a direction generally perpendicular to the direction in which it is produced, as opposed to "machine direction" which refers to the length of a fabric in the direction in which it is produced.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 40 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Film" refers to a thermoplastic or thermoset film made using a film extrusion and/or foaming process, such as a cast film or blown film extrusion process. For the purposes of the present invention, the term includes monolithic (nonporous) films as well as breathable microporous films that act as liquid barriers.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Machine direction" refers to the length of a fabric in the direction in which it is produced, as opposed to "cross direction" which refers to the width of a fabric in a direction generally perpendicular to the machine direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention may be substantially continuous in length.

"Nonwoven" and "nonwoven web" refer to fibrous materials and webs of fibrous material which are formed without the aid of a textile weaving or knitting process.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. Nos. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" or "extensible" means that a material can be stretched, without breaking, by at least 50% (to at least 150% of its initial (unstretched) length) in at least one direction, suitably by at least 70% (to at least 170% of its initial length), desirably by at least 100% (to at least 200% of its initial length). The term includes elastic materials as well as materials that stretch but do not significantly retract.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature. These terms may be defined with additional language in the remaining portions of the specification.

DETAILED DESCRIPTION OF THE PRESENTLY PREFERRED EMBODIMENTS

The present invention is directed to a biaxial elastic stretch, breathable laminate having cloth-like aesthetics and a fluid barrier. The material of the present invention is particularly suitable for use as an outer cover for disposable absorbent articles. Examples of such suitable articles include diapers, training pants, incontinence products, swim wear, other personal care or health care garments, or the like.

Figure 1:
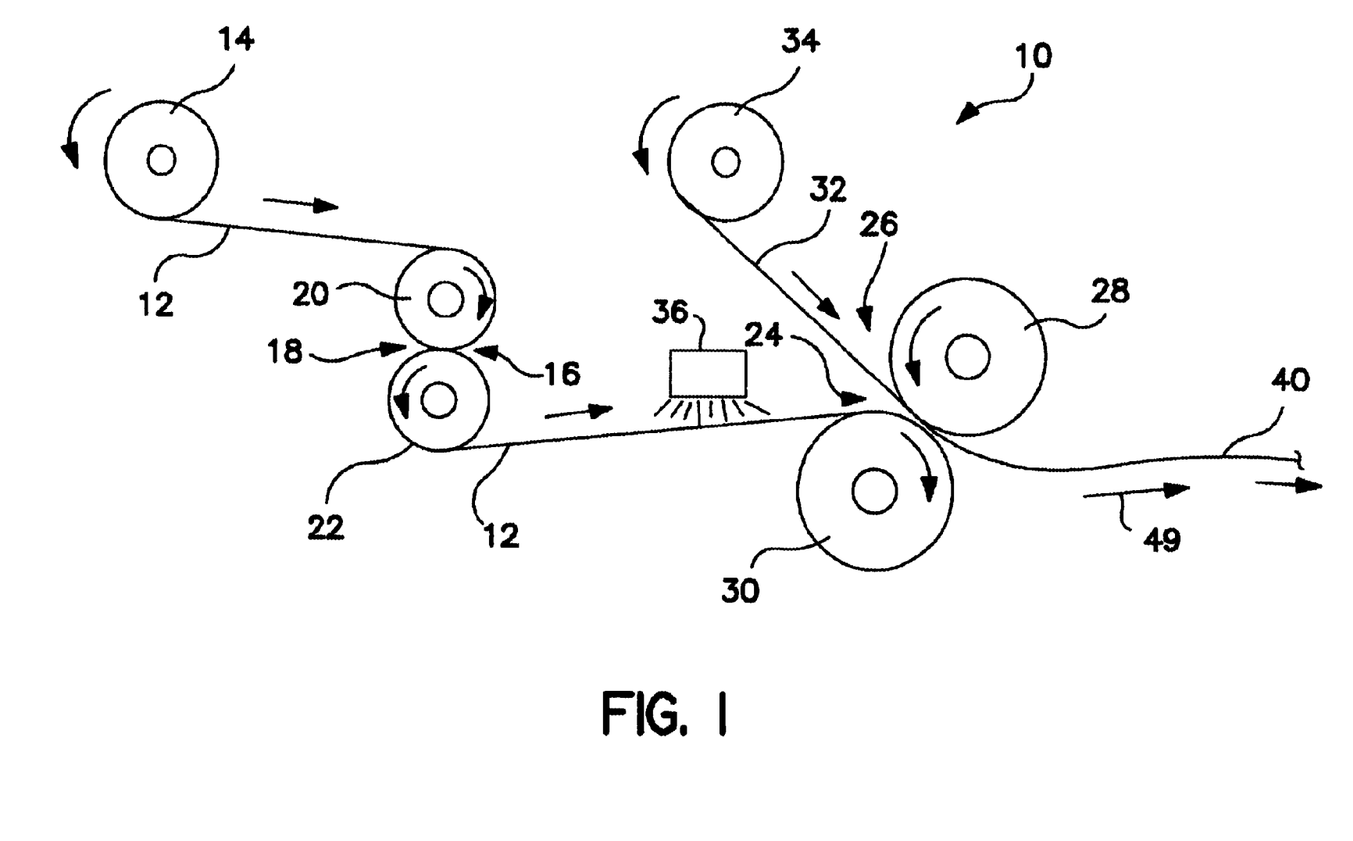
FIG. 1 is a schematic representation of an exemplary process for forming a composite cloth-like fluid barrier that delivers elasticity in multiple directions and has a controlled level of breathability.

Referring to FIG. 1, there is schematically illustrated at 10 a process for forming a biaxial elastic stretch, breathable laminate 40 having cloth-like aesthetics and a fluid barrier. A nonwoven facing material 12 is unwound from a supply roll 14 and travels in the direction indicated by the arrow associated therewith as the supply roll 14 rotates in the direction of the arrows associated therewith. The nonwoven facing material 12 passes through a nip 16 of the drive roller arrangement 18 formed by the drive rollers 20 and 22, and then toward a nip 24 of the bonder roller arrangement 26 formed by the bonder rollers 28, 30 where the material 12 meets and is bonded to a breathable elastic film 32.

The nonwoven facing material 12 may be a spunbond web and may be formed by known spunbonding processes. The nonwoven material 12 may also be a meltblown web, an air laid web, a bonded carded web, or a laminate of two or more nonwoven layers. The material 12 may be passed directly through the nip 16 without first being stored on a supply roll. The nonwoven material 12 may be rendered extensible in both the machine and cross directions as explained further below, and may or may not be elastic. The nonwoven facing material 12 provides a cloth-like feel and appearance on the laminate of the invention.

The breathable elastic film 32 can be unwound from a supply roll 34 and travels in the direction indicated by the arrow associated therewith as the supply roll 34 rotates in the direction of the arrows associated therewith. The breathable elastic film 32 passes through the nip 24 of the bonder roller arrangement 26 formed by the bonder rollers 28 and 30. The breathable elastic film 32 may be formed by extrusion processes such as, for example, film extrusion processes, and passed directly through the nip 24 without first being stored on a supply roll. The elastic film 32 may be stretched in one direction (e.g. the machine direction) prior to bonding to the nonwoven material 12, as explained further below.

A bonding device 36 bonds the facing material 12 to the breathable elastic film 32 at multiple, spaced apart locations, as the material 12 and the film 32 approach the nip 24 of the bonder roller arrangement 26. Thus, once the facing material 12 and the breathable elastic film 32 are bonded together and are passed through the bonder roller arrangement 26, a biaxial elastic stretch, breathable laminate 40 having cloth-like aesthetics and a fluid barrier is provided. In order to achieve the biaxial elastic stretch of the laminate 40, the facing material 12 can be a material having biaxial stretch and the breathable film 32 is elastic. The biaxial stretch facing material 12 bonded to the breathable elastic film 32 results in a biaxial elastic stretch, breathable laminate 40.

As indicated, several different combinations of facing materials 12 and breathable elastic films 32 can be used to produce the biaxial elastic stretch, breathable laminate 40 of the invention. First of all, the nonwoven facing material 12 can be an elastomeric spunbond web that is stretchable in both the machine direction and the cross direction. When such a facing material 12 is bonded to a film 32 that is elastomeric in both the machine direction and the cross direction, a biaxial elastic stretch, breathable laminate 40 is produced.

A second combination of facing material 12 and breathable elastic film 32 is a nonwoven facing material 12 that is necked in the machine direction, thereby imparting cross directional stretch to the material 12. Alternatively, a grooved roll extension process can be used to impart cross directional stretch to the material 12. The process of necking is described in U.S. Pat. No. 5,226,992 issued to Morman, hereby incorporated by reference. The necked material 12 can be bonded at multiple spaced-apart locations to an elastic film 32 that is pre-stretched in the machine direction. After the necked material 12 and the film 32 are bonded, the resulting composite 40 can be allowed to retract, thereby yielding recoverable machine and cross direction elasticity.

In yet another combination of facing material 12 and elastic film 32, the nonwoven facing material 12 is necked in the machine direction to achieve cross direction stretch, and is also creped or crimped in the machine direction to achieve machine direction stretch. The facing material 12 with imparted machine and cross direction stretch can be bonded to an elastic film 32 that is elastomeric in both the machine direction and the cross direction, thereby imparting machine and cross direction elasticity to the resulting laminate 40. Techniques of crimping are known in the art. One technique of creping is taught, for example, in U.S. Pat. No. 4,810,556, issued to Kobayashi et al., hereby incorporated by reference. Essentially, the creping process involves coating a nonwoven fabric with a lubricant and then pressing the coated fabric between a drive roll and a plate having a rough sandpaper-like surface. The nonwoven fabric is crinkled in a wavelike fashion in the direction of movement of the fabric by the frictional force caused by the pressing.

The term "cross direction," as used herein, refers to the width of a material in a direction generally perpendicular to the direction in which it is produced, as opposed to "machine direction," which refers to the length of a material in the direction in which it is produced. For reference, arrow 49 depicts the machine direction in FIGS. 1 and 2, while the cross direction in FIGS. 1 and 2 is essentially perpendicular to the plane of the figures thereby extending into and out of the page.

Figure 2:
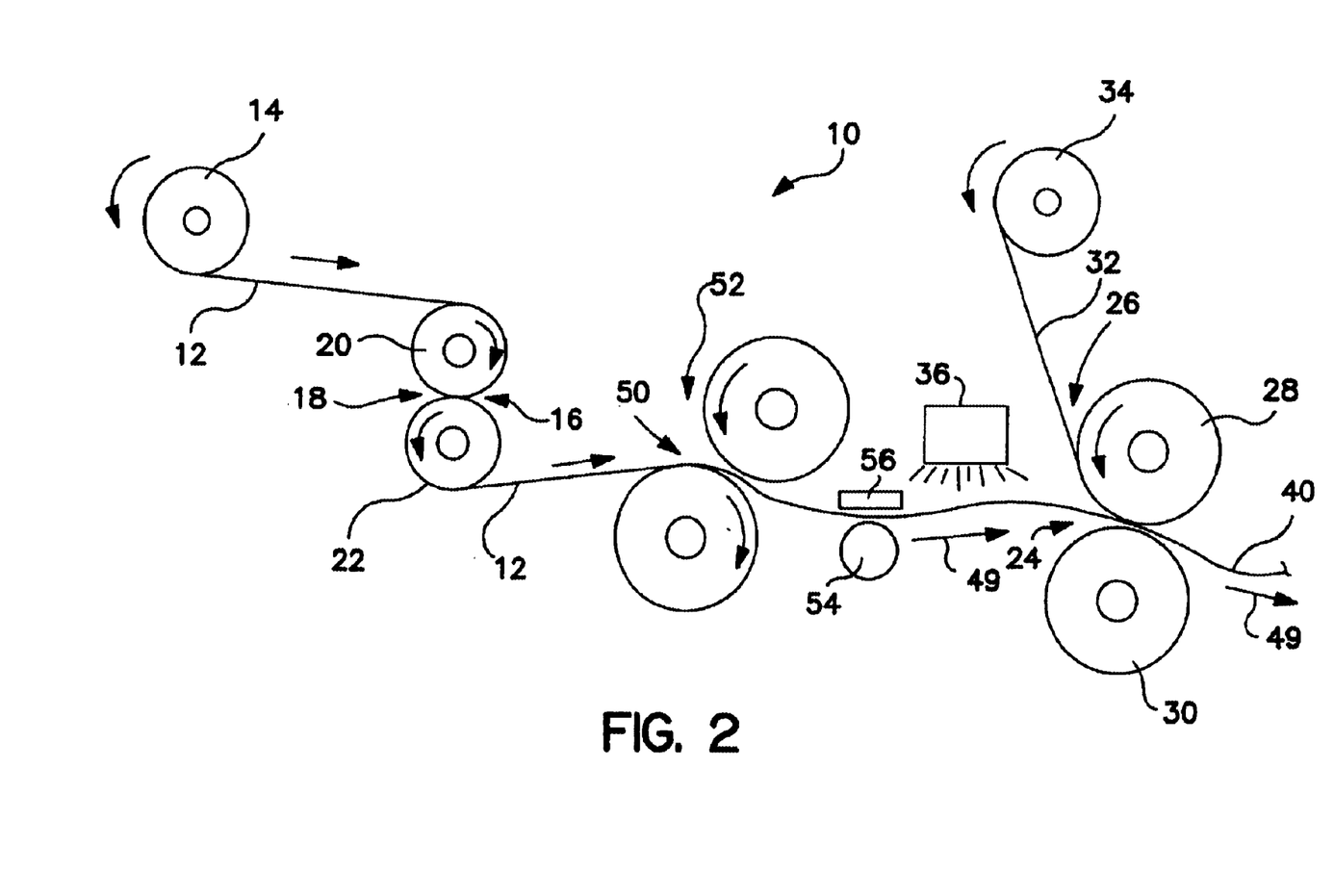
FIG. 2 is another schematic of an exemplary process for forming a composite cloth-like fluid barrier that delivers elasticity in multiple directions and has a controlled level of breathability.

In the process shown in FIG. 2, the facing material 12 passes through the nip 16 of the S-roll arrangement 18 in a reverse S-path as indicated by the rotation direction arrows associated with the stack rollers 20 and 22. From the S-roll arrangement 18, the facing material 12 passes through a pressure nip 50 formed by a neck roller arrangement 52. The peripheral linear speed of the rollers of the S-roll arrangement 18 can be controlled to be less than the peripheral linear speed of the rollers of the neck roller arrangement 52, such that the facing material 12 is tensioned between the S-roll arrangement 18 and the pressure nip of the neck roll arrangement 52. By adjusting the difference in the speeds of the rollers, the facing material 12 can be tensioned so that it necks a desired amount and is then coated with a lubricant and pressed between a drive roll 54 and a plate 56 having a rough sandpaper-like surface, in accordance with the creping process. The facing material 12 having mechanically manipulated machine direction and cross direction stretchability is then joined to the breathable elastic film 32 during their passage through a bonder roller arrangement 26 to form a biaxial elastic stretch, breathable laminate 40.

Conventional drive means and other conventional devices which may be utilized in conjunction with the apparatus of FIGS. 1 and 2 are well known and, for purposes of clarity, have not been illustrated in the schematic views of FIGS. 1 and 2.

If the nonwoven facing material 12 is necked, fibers of the material 12 should be joined by interfiber bonding to form a coherent web structure which is able to withstand necking. Interfiber bonding may be produced by entanglement between individual meltblown fibers. The fiber entangling is inherent in the meltblown process but may be generated or increased by processes such as, for example, hydraulic entangling or needlepunching. Alternatively and/or additionally a bonding agent may be used to increase the desired bonding. A spunbond web has interfiber bonding caused by thermal bonding for the fibers in the spunbonding process.

Suitably, the facing material 12 can be a spunbond web including a thermoplastic elastomer. As mentioned, the facing material 12 can be machine direction and cross direction stretchable. For example, the facing material 12 can be a side by side bi-component spunbond fiber having a primary side and a secondary side. The primary side can include polypropylene and the secondary side can include a polymer that quenches in a differential manner than polypropylene, such as a flexible polyolefin. Useful polypropylenes include, for example, polypropylene available from the Exxon Chemical Company under the trade designation Exxon 3445, and polypropylene available from the Shell Chemical Company under the trade designation DX 5A09.

The facing material 12 can be elastic in nature, for example, as a spunbond nonwoven produced from a thermoplastic elastomer creating an elastic fiber matrix. Materials suitable for use in preparing an elastic facing material 12 include diblock, triblock, or multi-block elastomeric copolymers, including styrene-isoprenestyrene, styrene-butadiene-styrene, styrene-ethylene/butylene-styrene, or styrene-ethylene/propylene-styrene, which may be obtained from the Shell Chemical Company, under the trade designation KRATON® elastomeric resin; polyurethanes, including those available from E.I. Du Pont de Nemours Co., under the trade name LYCRA® polyurethane; polyamides, including polyether block amides available from Ato Chemical Company, under the trade name PEBAX® polyether block amide; polyesters, such as those available from E.I. Du Pont de Nemours Co., under the trade name HYTREL® polyester, and single-site or metallocene-catalzed polyolefins having density less than about 0.89 grams/cc, available from Dow Chemical Co. under the trade name AFFINITY®.

A number of block copolymers can be used to prepare the elastic facing material 12 useful in this invention. Such block copolymers generally comprise an elastomeric midblock portion and a thermoplastic endblock portion. The block copolymers used in this invention generally have a three-dimensional physical crosslinked structure and are elastomeric below the endblock portion glass transition temperature ($T_2$). The block copolymers are also thermoplastic in the sense that they can be melted, formed, and resolidified several times with little or no change in physical properties (assuming a minimum of oxidative degradation).

One way of synthesizing such block copolymers is to polymerize the thermoplastic endblock portions separately from the elastomeric midblock portions. Once the midblock and endblock portions have been separately formed, they can be linked. Typically, midblock portions can be obtained by polymerizing di- and tri-unsaturated $C_4$–$C_{10}$ hydrocarbons such as, for example, dienes such as butadiene, isoprene, and the like, and trienes such as 1, 3, 5-heptatriene, and the like. When an endblock portion A is joined to a midblock portion B, an A-B block copolymer unit is formed, which unit can be coupled by various techniques or with various coupling agents C to provide a structure such as A-B-A, which is believed to comprise two A-B blocks joined together in a tail-to-tail A-B-C-B-A arrangement. By a similar technique, a radial block copolymer can be formed having the formula $(A-B)_nC$, wherein C is the hub or central polyfunctional coupling agent and n is a number greater than 2. Using the coupling agent technique, the functionality of C determines the number of A-B branches.

Endblock portion A generally comprises a poly (vinylarene), such as polystyrene, having an average molecular weight between 1,000 and 60,000. Midblock portion B generally comprises a substantially amorphous polyolefin such as polyisoprene, ethylene/propylene polymers, ethylene/butylene polymers, polybutadiene, and the like, or mixtures thereof, having an average molecular weight between about 5,000 and about 450,000. The total molecular weight of the block copolymer is suitably about 10,000 to about 500,000 and more suitably about 200,000 to about 300,000. Any residual unsaturation in the midblock portion of the block copolymer can be hydrogenated selectively so that the content of olefinic double bonds in the block copolymers can be reduced to a residual proportion of less than 5 percent and suitably less than about 2 percent. Such hydrogenation tends to reduce sensitivity to oxidative degradation and may have beneficial effects upon elastomeric properties.

Suitable block copolymers used in this invention comprise at least two substantially polystyrene endblock portions and at least one substantially ethylene/butylene midblock portion. As an example, ethylene/butylene typically may comprise the major amount of the repeating units in such a block copolymer and can constitute, for example, 70 percent by weight or more of the block copolymer. The block copolymer can have three or more arms, and good results can be obtained with, for example, four, five, or six arms. The midblock portion can be hydrogenated, if desired.

Linear block copolymers, such as A-B-A, A-B-A-B-A or the like, are suitably selected on the basis of endblock content, larger endblocks being preferred. For polystyrene-ethylene/butylene-polystyrene block copolymers, a styrene content in excess of about 10 percent is suitable, such as between about 12 to about 30 weight percent. With higher styrene content, the polystyrene endblock portions generally have a relatively high molecular weight. A commercially available example of such a linear block copolymer is a styrene-ethylene/butylene-styrene block copolymer which contains about 13 weight percent styrene units and essentially the balance being ethylene/butylene units, commercially available from the Shell Chemical Company, under the trade designation KRATON® G1657 elastomeric resin. Typical properties of KRATON® G1657 elastomeric resin are reported to include a tensile strength of 3400 pounds per square inch ($2\times10^6$ kilograms per square meter), a 300 percent modulus of 350 pounds per square inch ($1.4\times10^5$ kilograms per square meter), an elongation of 750 percent at break, a Shore A hardness of 65, and a Brookfield viscosity, when at a concentration of 25 weight percent in a toluene solution, of about 4200 centipoise at room temperature. Another suitable elastomer, KRATON® G2740, is a styrene butadiene block copolymer blended with tackifier and low density polyethylene.

Other suitable elastomeric polymers may also be used to make the elastic facing material 12. These include, without limitation, elastomeric (single-site or metallocene catalyzed) polypropylene, polyethylene and other alpha-olefin homopolymers and copolymers, having density less than about 0.89 grams/cc; ethylene vinyl acetate copolymers; and substantially amorphous copolymers and terpolymers of ethylene-propylene, butene-propylene, and ethylene-propylene-butene.

Metallocene-catalyzed elastomeric polymers are relatively new, and may be presently preferred. The metallocene process for making polyolefins uses a metallocene catalyst which is activated (i.e., ionized) by a co-catalyst.

Polymers produced using metallocene catalysts have a narrow molecular weight distribution. "Narrow molecular weight distribution polymer" refers to a polymer that exhibits a molecular weight distribution of less than about 3.5. As is known in the art, the molecular weight distribution of a polymer is the ratio of the weight average molecular weight of the polymer to the number average molecular weight of the polymer. Methods of determining molecular weight distribution are described in the *Encyclopedia of Polymer Science and Engineering*, Volume 3, Pages 299–300 (1985). Examples of narrow molecular weight distribution polyolefins include the metallocene-catalyzed polyolefins, the single-site catalyzed polyolefins, and the constrained geometry-catalyzed polyolefins described above. As is known in the art, the metallocene-catalyzed polyolefins and the constrained geometry-catalyzed polyolefins are sometimes referred to as types of single-site catalyzed polymers. Polydispersities ($M_w/M_n$), of below 3.5 and as even below 2 are possible for metallocene produced polymers. These polymers also have a narrow short chain branching distribution when compared to otherwise similar Ziegler-Natta produced polymers.

Metallocene catalysts include bis(n-butylcyclopentadienyl) titanium dichloride, bis(n-butylcyclopentadienyl)zirconium dichloride, bis (cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl (cyclopentadienyl$_1$,-1-flourenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow.

The metallocene process, and particularly the catalysts and catalyst support systems are the subject of a number of patents. U.S. Pat. No. 4,542,199 to Kaminsky et al. describes a procedure wherein a metallocene catalyst of the general formula (cyclopentadienyl)2MeRHal wherein Me is a transition metal, Hal is a halogen and R is cyclopentadienyl or a C1 to C6 alkyl radical or a halogen, is used to form polyethylene. U.S. Pat. No. 5,189,192 to LaPointe et al. and assigned to Dow Chemical describes a process for preparing addition polymerization catalysts via metal center oxidation. U.S. Pat. 5,352,749 to Exxon Chemical Patents, Inc. describes a method for polymerizing monomers in fluidized beds. U.S. Pat. No. 5,349,100 describes chiral metallocene compounds and preparation thereof by creation of a chiral center by enantioselective hydride transfer.

Co-catalysts are materials such as methylaluminoxane (MAO) which is the most common, other alkylaluminums and boron containing compounds like tris (pentafluorophenyl)boron, lithium tetrakis (pentafluorophenyl)boron, and dimethylanilinium tetrakis (pentafluorophenyl)boron. Research is continuing on other co-catalyst systems or the possibility of minimizing or even eliminating the alkylaluminums because of handling and product contamination issues. The important pont is that the metallocene catalyst be activated or ionized to a cationic form for reaction with the monomer(s) to be polymerized.

Commercial production of metallocene polymers is somewhat limited but growing. Such polymers are available from Exxon Chemical Company of Baytown, Tex. under the trade name EXXPOL® for polypropylene based polymers and EXACT® for polyethylene based polymers. Dow Chemical Company of Midland, Mich. has polymers commercially available under the name ENGAGE®. These materials are believed to be produced using non-stereo selective metallocene catalysts. Exxon generally refers to their metallocene catalyst technology as "single site" catalysts while Dow refers to theirs as "constrained geometry" catalysts under the name INSIGHT® to distinguish them from traditional Ziegler-Natta catalysts which have multiple reaction sites. Other manufacturers such as Fina Oil, BASF, Amoco, Hoechst and Mobil are active in this area and it is believed that the availability of polymers produced according to this technology will grow substantially in the next decade.

Regarding metallocene based elastomeric polymers, U.S. Pat. No. 5,204,429 to Kaminsky et al. describes a process which may produce elastic copolymers from cycloolefins and linear olefins using a catalyst which is a stereorigid chiral metallocene transition metal compound and an aluminoxane. The polymerization is carried out in an inert solvent such as an aliphatic or cycloaliphatic hydrocarbon such as toluene. The reaction may also occur in the gas phase using the monomers to be polymerized as the solvent. U.S. Pat. Nos. 5,278,272 and 5,272,236, both to Lai et al., assigned to Dow Chemical and entitled "Elastic Substantially Linear Olefin Polymers" describe polymers having particular elastic properties. Dow also commercially produces a line of elastomeric polyolefins under the trade name ENGAGE®.

The elastomeric fibers may be substantially continuous or staple in length, but are preferably substantially continuous. Substantially continuous filaments exhibit better containment of the cellulose fibers and superabsorbent material, have better elastic recovery and provide better distribution of liquids, than staple length fibers. The elastomeric fibers may be produced using a spunbonding process, a meltblowing process, or another suitable process. The elastomeric fibers may have an average diameter of about 1–75 microns, preferably about 1–40 microns, more preferably about 1–30 microns.

The facing material 12 may also be a composite material made of a mixture of two or more different fibers or a mixture of fibers and particulates. Such mixtures may be formed by adding fibers and/or particulates to the gas stream in which meltblown fibers are carried so that an intimate entangled commingling of meltblown fibers and other materials, e.g., wood pulp, staple fibers and particulates such as, for example, hydrocolloid (hydrogel) particulates commonly referred to as superabsorbent materials, occurs prior to collection of the meltblown fibers upon a collecting device to form a coherent web of randomly dispersed meltblown fibers and other materials such as disclosed in U.S. Pat. No. 4,100,324, the disclosure of which is hereby incorporated by reference.

The breathable elastic film 32 is suitably liquid impermeable and water-vapor permeable, thereby providing a positive barrier to liquids while still allowing water vapor to pass through. A suitable liquid impermeable film is a 0.2 millimeter polyethylene film commercially available from Huntsman Packaging of Newport News, Va., U.S.A. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. The breathable elastic film 32 can be embossed and/or matte finished to provide a more cloth-like appearance.

The breathable elastic film 32 suitably includes an elastomeric polymer, such as a microporous elastomer. Typically, such breathable elastic films are lightweight, having a basis weight in a range of about 5 to 20 grams per square meter. Low basis weight films are advantageous because of higher breathability and economic reasons, and are particularly useful in disposable products. Additionally, elastic sheets having higher basis weights such as, for example, from about 21 to about 100 grams per square meter may also be used.

The breathable elastic film 32 is suitably made from a water vapor-permeable polymer and should have a water vapor transmission rate (WVTR) above about 500 grams/$m^2$—24 hours, suitably in a range of about 750 to 50,000 grams/$m^2$—24 hours, using most suitably in a range of about 1,000 to 40,000 grams/$m^2$—24 hours, using the Mocon WVTR test procedure described below. The WVTR is a function of both film thickness and polymer type. Preferred polymers which exhibit the required WVTR over a range of useful film thicknesses include without limitation thermoplastic polyurethanes, polyether amides, polyester elastomers, and combinations thereof. Several examples of elastomeric thermoplastic polyurethanes, polyether amides and polyester elastomers are listed above, including PEBAX® polyether block amide and HYTREL® polyester.

In addition to being water vapor-permeable, the breathable elastic film 32 should not be so thick as to substantially impair its water vapor transmission. For a monolithic film made using a breathable polymer, the WVTR of a particular composition of film is roughly inversely related to its thickness. Polymers having somewhat lower water vapor permeability than the ranges listed should therefore be made into thinner films in order to achieve suitable vapor transmission. For instance, the vapor permeable film may be less than about 25.4 microns thick, or less than about 12.7 microns thick, or less than about 7.62 microns thick depending on the strength of the film and the water vapor permeability of the polymer.

The water vapor-permeable polymer films may be crosslinked or thermoplastic, depending on the polymer. The crosslinking can be accomplished by applying heat treatment such as by placing films in an oven. Polyurethanes may be thermoplastic or crosslinked. Polyether amides and polyester elastomers are generally thermoplastic.

The breathable elastic film 32 may also be a multilayer material in that it may include two or more individual coherent webs or films. Additionally, the breathable elastic film 32 may be a multilayer material in which one or more of the layers contain a mixture of elastic and nonelastic fibers or particulates.

The facing material 12 component of the laminate 40 is typically open and porous, and does not significantly affect the breathability of the laminate 40. In other words, the moisture breathability of the film 32 should determine the breathability of the laminate 40. However, care should be taken to bond the film 32 and facing material 12 together using techniques that do not significantly disrupt the breathability of the laminate 40. If an adhesive is used, the adhesive should cover only a portion of the total film area, and should be applied as thinly as possible. The preferred adhesive for attaching polyurethane films to a spunbonded web, for example, is a reactive polyurethane-based adhesive available from Shawmut Mills in Bridgewater, Mass. When used, an adhesive should be applied at a basis weight less than about 10.0 grams per square meter (gsm), suitably less than about 5.0 gsm, most suitably less than about 1.0 gsm. The adhesive should suitably cover not more than about 75% of the film surface unless the adhesive itself is very water permeable. Furthermore, any type of bonding that is used, whether it is adhesive, thermal, or any other type, the bonding is suitably discontinuous, thereby bonding the facing material 12 to the film 32 in multiple, spaced apart locations. The discontinuous bonding does not inhibit or restrict simultaneous movement of the layers the way continuous bonding does, particularly when the film 32 is elastomeric and the facing material 12 is stretchable but does not retract on its own.

Figure 3:
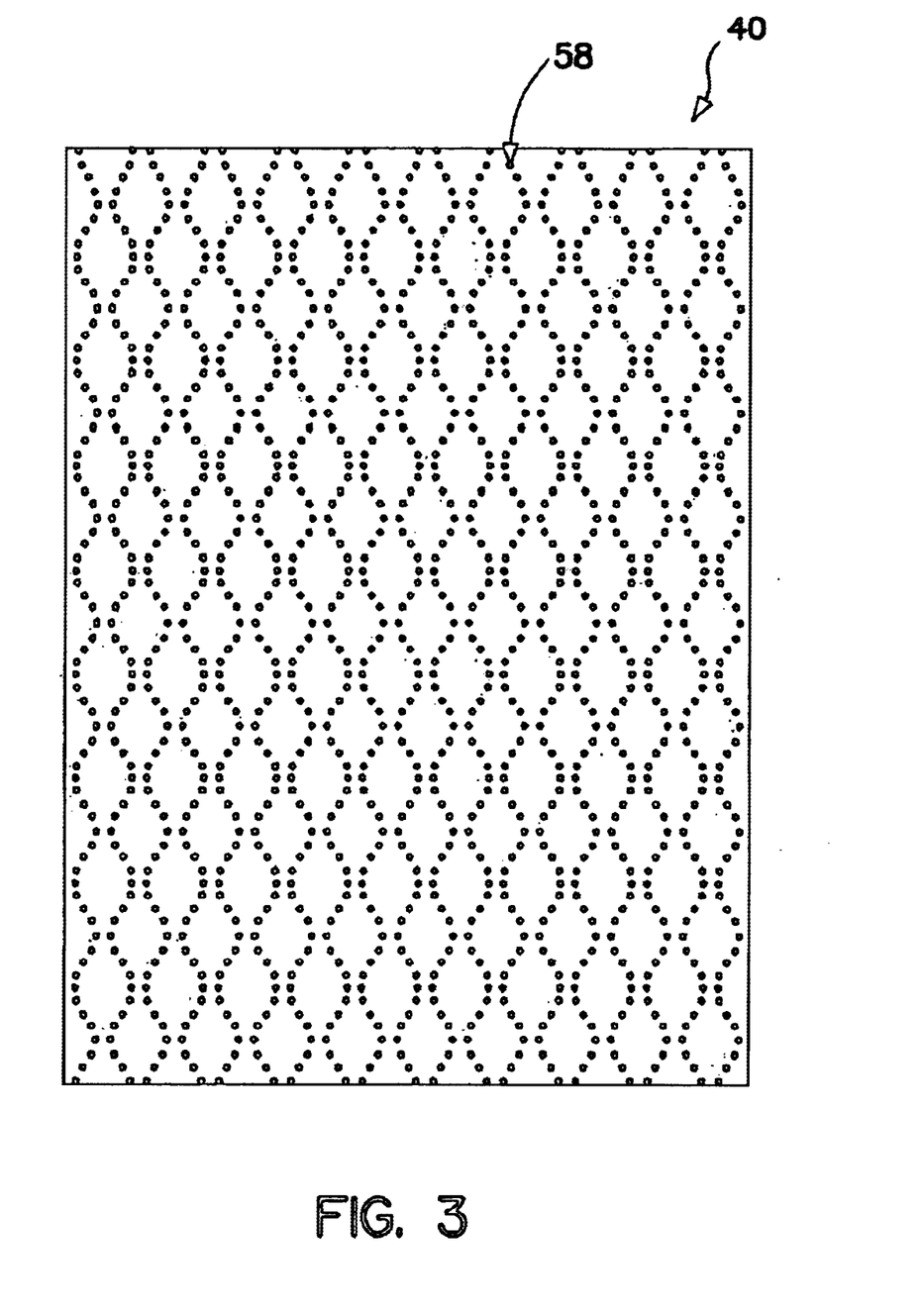
FIG. 3 shows a sinusoidal bonding pattern.
Figure 4:
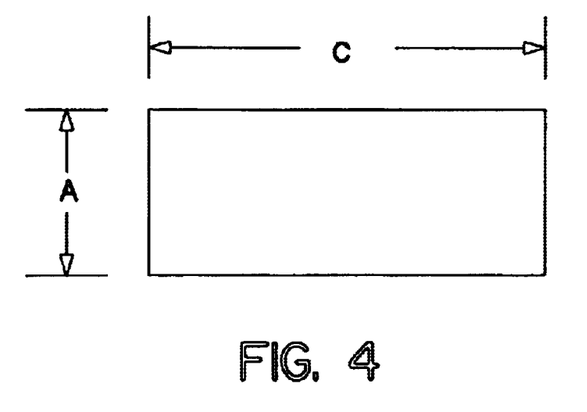
FIG. 4 is a representation plan view of an exemplary facing material before tensioning and necking.
Figure 5:
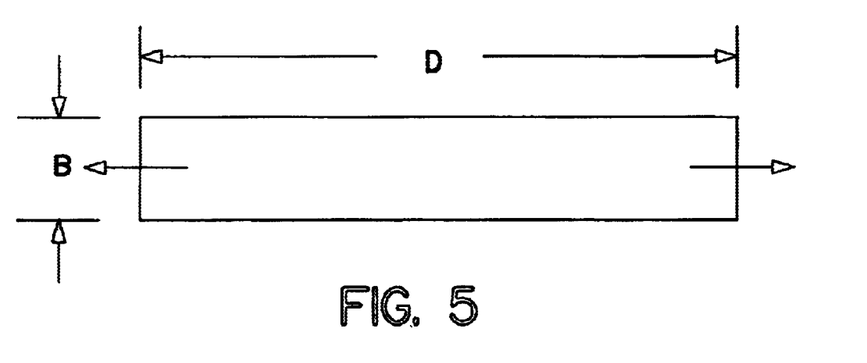
FIG. 5 is a plan view of an exemplary facing material necked in a machine direction.

When thermal bonding is employed, the bonding conditions should be such that the facing material 12 is not unnecessarily compressed or fused together, and the film 32 is not damaged or distorted in a way that significantly impairs moisture breathability. Thermal calender bonding is a preferred technique, using a spaced apart bond pattern that attaches the web 12 and film 32 together at less than about 25% of the total interfacial area, preferably less than about 20% of the total interfacial area, most preferably less than about 15% of the total interfacial area. A sinusoidal bond pattern 58 is shown, for example, in FIG. 3. This pattern 58 has approximately 75 pins per square inch with each pin about 0.059 inches in diameter, providing a bond surface area of about 20.5 percent.

With regard to thermal bonding, one skilled in the art will appreciate that the temperature to which the materials, or at least the bond sites thereof, are heated for heat-bonding will depend not only on the temperature of the heated roll(s) or other heat sources but on the residence time of the materials on the heated surfaces, the basis weights of the materials and their specific heats and thermal conductivities. However, for a given combination of materials, and in view of the herein contained disclosure the processing conditions necessary to achieve satisfactory bonding can be readily determined by one of skill in the art.

Another suitable method of bonding the facing material 12 and the film 32 together includes an extrusion coating process, wherein the film 32 is extruded in a molten state onto the facing material 12 in a thin layer.

The relation between the original dimensions of the facing material 12 to its dimensions after tensioning determines the approximate limits of stretch of the composite biaxial elastic stretch, breathable material 40. Because the facing material 12 is able to stretch and return to its unstretched dimensions in directions such as, for example the machine direction and the cross direction, the composite biaxial elastic stretch, breathable material 40 will be stretchable in generally the same direction as the facing material 12.

Figure 6:
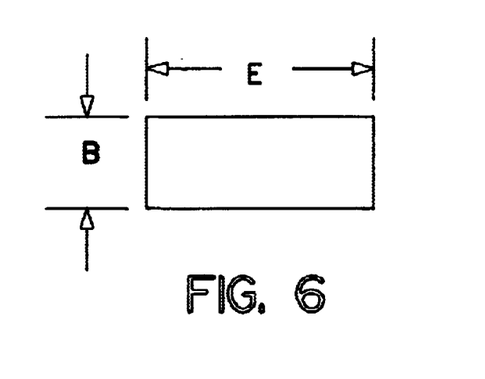
FIG. 6 is a plan view of an exemplary facing material necked in a cross direction.
Figure 7:
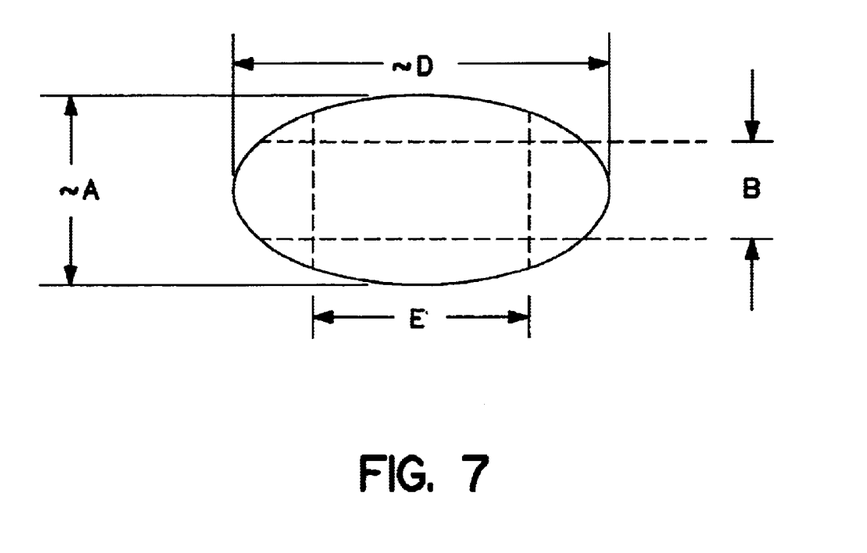
FIG. 7 is a plan view of an exemplary composite material while partially stretched in the cross direction and the machine direction.

For example, with reference to FIGS. 4, 5, 6, and 7, if it is desired to prepare a composite biaxial elastic stretch, breathable material 40 that is stretchable to about 150% of its initial width in the cross direction and to about 150% of its initial length in the machine direction. A piece of facing material shown schematically and not necessarily to scale in FIG. 4 having a width "A" such as, for example, 250 cm, and a length "C" of, for example, 400 cm, is tensioned so that it necks down to a width "B" of about 100 cm and lengthens to a length "D" of about 500 cm, shown in FIG. 5. This necked material is then heat set to make a reversibly necked spunbond as taught in U.S. Pat. No. 4,965,122, issued to Morman and hereby incorporated by reference. The facing material shown in FIG. 5 has a length "D" of about 500 cm, as mentioned, and is creped or otherwise retracted to a length "E" of about 200 cm, shown in FIG. 6. The resulting facing material shown in FIG. 6 is then joined to a breathable elastic film (not shown) having a width of approximately 100 cm which is at least stretchable to a width of 250 cm, and having a length of approximately 200 cm which is at least stretchable to a length of 500 cm. The resulting composite biaxial elastic stretch, breathable material shown schematically and not necessarily to scale in FIG. 7 has a width "B" of about 100 cm and is stretchable to at least the original 250 cm width "A" of the facing material for a cross direction elongation of about 150%, and a length "E" of about 200 cm and is stretchable to at least the 500 cm length "D" of the lengthened facing material for a machine direction elongation of about 150%. As can be seen from the example, the elastic limit of the breathable film needs only to be as great as the minimum desired elastic limit of the composite biaxial elastic stretch, breathable material.

Suitably, the biaxial elastic stretch, breathable laminate of the invention can stretch more than about 50% in the machine direction, more suitably between about 70% and 200%, most suitably between about 100% and 150%. Similarly, the stretchability of the laminate in the cross direction is suitably more than about 50% in the cross direction, more suitably between about 70% and 200%, most suitably between about 100% and 150%. The laminate suitably recovers at least 40% of its elongation upon retraction in both the machine direction and the cross direction, more suitably at least 50% of its elongation is recovered. Elastic tensions are generally determined by the type and basis weight of the film component, however, the facing type and lamination method can impact tension properties, permanent set and hysteresis properties of the resulting laminate. As a result, machine direction and cross direction properties can be altered by the type of facing and lamination technique used. Suitably, a very "square" laminate, i.e., a laminate with similar machine direction and cross direction elastic properties, can be formed.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

Test Procedure For Water Vapor Transmission Rate (WVTR)

A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modern Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer than calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material,\ guardfilm,\ airgap} - TR^{-1}_{guardfilm,\ airgap}$$

Calculations:
WVTR: The calculation of the WVTR uses the formula:

$$WVTR = F p_{sat}(T)RH/A p_{sat}(T)(1-RH))$$

where:

F = The flow of water vapor in cc/min., $P_{sat}(T)$ = The density of water in saturated air at temperature T, RH = The relative humidity at specified locations in the cell, A = The cross sectional area of the cell, and, $P_{sat}(T)$ = The saturation vapor pressure of water vapor at temperature T.

We claim:

1. A biaxial elastic stretch, breathable laminate, consisting essentially of:

a water vapor-permeable elastic film comprising a polymer selected from a group consisting of polyurethanes, polyether amides, polyester elastomers and combinations thereof; and a spunbond nonwoven web, having machine direction stretch and cross direction stretch, bonded to the film, wherein the spunbond nonwoven web is creped without the use of intermediate fixing steps to achieve the machine direction stretch and bonded to the elastic film whereby the film has a water vapor transmission rate of at least about 500 grams/m$^2$—24 hours; wherein spunbond nonwoven web comprises a side by side bi-component spunbond fiber having a primary side and a secondary side and wherein the primary side comprises polypropylene and the secondary side comprises a polymer that quenches in a differential manner than polypropylene.

2. The laminate of claim 1, wherein the film and web are thermally bonded together.

3. The laminate of claim 1, wherein the film and web are adhesively bonded together.

4. The laminate of claim 1, wherein the film and web are bonded together via an extrusion coating process.

5. The laminate of claim 1, wherein stretchability of the laminate in a machine direction is at least 50%.

6. The laminate of claim 1, wherein stretchability of the laminate in a machine direction is in a range of 70% to 200%.

7. The laminate of claim 1, wherein stretchability of the laminate in a machine direction is in a range of 100% to 150%.

8. The laminate of claim 1, wherein stretchability of the laminate in a cross direction is at least 50%.

9. The laminate of claim 1, wherein stretchability of the laminate in a cross direction is in a range of 70% to 200%.

10. The laminate of claim 1, wherein stretchability of the laminate in a cross direction is in a range of 100% to 150%.

11. The laminate of claim 1, wherein stretchability of the laminate in a machine direction is roughly equal to stretchability of the laminate in a cross direction.

12. An absorbent article outer cover comprising the laminate of claim 1.

13. A biaxial elastic stretch, breathable laminate fluid barrier, consisting essentially of:

a breathable elastic film; and a necked nonwoven facing material that is creped in the machine direction without the use of intermediate fixing steps to allow for machine direction stretch and subsequently bonded to the film whereby the film has a water vapor transmission rate of at least about 500 grams/m$^2$—24 hours; and wherein the facing material comprises a side by side bi-component spunbond fiber having a primary side and a secondary side and wherein the primary side comprises polypropylene and the secondary side comprises a polymer that quenches in a differential manner than polypropylene.

14. A biaxial elastic stretch, breathable laminate fluid barrier, comprising:

a breathable elastic film; and a necked nonwoven facing material that is creped in the machine direction without the use of intermediate fixing steps to allow for machine direction stretch and subsequently bonded to the film; and wherein the facing material comprises a side by side bi-component spunbond fiber having a primary side and a secondary side and wherein the primary side comprises polypropylene and the secondary side comprises a polymer that quenches in a differential manner than polypropylene; and wherein the film is pre-stretched when bonded to the facing material and whereby the film has a water vapor transmission rate of at least about 500 grams/m$^2$—24 hours.

15. The laminate of claim 13, wherein the film comprises a thermoplastic polyurethane.

16. The laminate of claim 13, wherein the film comprises a polyether amide.

17. The laminate of claim 13, wherein the film comprises a polyester elastomer.

18. The laminate of claim 13, wherein the film comprises a monolithic film including a breathable polymer.

19. The laminate of claim 13, wherein the film comprises a breathable microporous film.

20. The laminate of claim 13, wherein the film has a water vapor transmission rate in a range of about 750 to about 50,000 grams/m$^2$—24 hours.

21. The laminate of claim 13, wherein the film has a water vapor transmission rate in a range of about 37,000 to about 40,000 grams/m$^2$—24 hours.

22. The laminate of claim 13, wherein the film has a basis weight in a range of 5 to 20 grams per square meter.

23. The laminate of claim 13, wherein the facing material is stretchable in a cross direction.

24. The laminate of claim 13, wherein the facing material is stretchable in a cross direction and in a machine direction.

25. The laminate of claim 13, wherein the facing material is elastomeric in a machine direction and in a cross direction.

26. The laminate of claim 13, wherein the polymer comprises a flexible polyolefin.

27. The laminate of claim 13, wherein the facing material comprises a spunbond nonwoven.

28. The laminate of claim 27, wherein the spunbond nonwoven comprises a thermoplastic elastomer.

29. The laminate of claim 13, wherein the facing material comprises a single site catalyzed elastomer.

30. The laminate of claim 13, wherein the facing material comprises a thermoplastic polyurethane.

31. The laminate of claim 1, wherein the polymer comprises a flexible polyolefin.

32. The laminate of claim 14, wherein the polymer comprises a flexible polyolefin.

* * * * *